US011497215B2

(12) United States Patent
Kong

(10) Patent No.: US 11,497,215 B2
(45) Date of Patent: *Nov. 15, 2022

(54) DEVICES, SYSTEMS AND METHODS OF MAKING AND USING CHLORINE DIOXIDE BASED FORMULATION WITH IMPROVED STABILITY

(71) Applicant: Spectrum Doxyicide LLC, Denver, CO (US)

(72) Inventor: Stephen Bradford Kong, Alamo, CA (US)

(73) Assignee: SPECTRUM DOXYICIDE, LLC, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/995,804

(22) Filed: Aug. 17, 2020

(65) Prior Publication Data

US 2020/0375192 A1 Dec. 3, 2020

Related U.S. Application Data

(63) Continuation-in-part of application No. 16/884,033, filed on May 26, 2020, which is a continuation-in-part of application No. 15/997,660, filed on Jun. 4, 2018, now Pat. No. 10,660,339.

(51) Int. Cl.
*A01N 59/00* (2006.01)
*A61L 2/18* (2006.01)

(52) U.S. Cl.
CPC .............. *A01N 59/00* (2013.01); *A61L 2/18* (2013.01)

(58) Field of Classification Search
CPC ..... A61L 2/18; A61L 2/22; A61L 9/14; A61L 2202/26; A01N 59/00
See application file for complete search history.

(56) References Cited

U.S. PATENT DOCUMENTS

| 9,788,549 | B2 * | 10/2017 | Wood ...................... A01N 59/00 |
| 10,660,339 | B2 * | 5/2020 | Kong ...................... A01N 59/08 |
| 2008/0226748 | A1 * | 9/2008 | Stevenson .............. A01N 59/00 424/665 |
| 2010/0015066 | A1 * | 1/2010 | Speronello .............. A61P 31/02 424/53 |
| 2015/0237864 | A1 * | 8/2015 | Wood ...................... A01N 59/00 424/661 |
| 2017/0360659 | A1 * | 12/2017 | Mundschau ............. A61K 8/25 |

FOREIGN PATENT DOCUMENTS

GB 2345637 A * 7/2000 ............... C11D 3/48

* cited by examiner

*Primary Examiner* — Blessing M Fubara
(74) *Attorney, Agent, or Firm* — Michael R Shevlin

(57) ABSTRACT

Disclosed are devices, systems, and methods for producing broad spectrum disinfectants, sanitizers, cleaner and deodorizers using chlorine dioxide compositions, and more particularly, to methods for producing chlorine dioxide compositions having improved long term stability by the proper choice of pH and through the careful choice of other product formula ingredients.

17 Claims, 5 Drawing Sheets

DEVICES, SYSTEMS AND METHODS OF MAKING AND USING CHLORINE DIOXIDE BASED FORMULATION WITH IMPROVED STABILITY

CROSS-REFERENCE TO RELATED APPLICATIONS

This application is a continuation-in-part to U.S. patent application Ser. No. 16/884,033, filed on May 26, 2020, which is a continuation-in-part to U.S. patent application Ser. No. 15/997,660, filed on Jun. 4, 2018, which is related to U.S. application Ser. No. 14/631,806 titled BROAD SPECTRUM DISINFECTANT, filed on Feb. 25, 2015, which claims priority to U.S. Provisional Application No. 61/945,054, filed Feb. 26, 2014, which are incorporated herein by reference.

FIELD

The present invention is generally related to broad spectrum disinfectants, sanitizers, cleaners or deodorizers using chlorine dioxide compositions, and more particularly, to methods for producing chlorine dioxide compositions having improved long term stability by the proper choice of pH and through the careful choice of other product formula ingredients.

BACKGROUND

For a product to be successful in the marketplace, it must have suitable shelf life stability, in addition to, providing the desired function and aesthetics. Disinfecting or sanitizing products require a suitable biocidal agent. Some examples of biocides are chlorine dioxide, hypochlorite, peroxide, and quaternary amines. Many products containing reactive ingredients such a chlorine dioxide (ClO2) have problems with long-term stability, thus limiting their shelf-life. Chlorine dioxide is an effective biocide and can clean and deodorize. One particular advantage of ClO2 over hypochlorite is that ClO2 does not chlorinate organic compounds. However, it is inherently less stable than other biocides such as quaternary amines. Due to instability, most applications involve producing chlorine dioxide at the source of use. Therefore, chlorine dioxide must be properly formulated to be viable.

Products containing chlorine dioxide generally have a limited shelf life because chlorine dioxide decomposes over time even in closed bottles. Typically, unstable products will have a use by or expiration date to ensure that the product's designated performance, such as micro efficacy, is maintained throughout the time period. Manufacturing and inventory control, as well as, maintaining microbiological efficacy are therefore challenging for product with limited lifetime. Due it its inherent instability, chlorine dioxide is often produced at the source using a chlorine dioxide generator. Another approach is to market a 2-Part (or multipart) product where the precursors of the active ingredients are mixed/reacted at the point of use, and then specify an appropriate time period to use the product. However, 2-Part products generally require more complex packaging, and require the consumer to perform an extra "mixing" step before using. There is also a risk that that the mixing/reacting step is not followed properly. This extra mixing step may not be desirable to the consumer and the consumer may prefer an alternative product. Yet another approach could be use a package and a trigger/pump dispenser system that keeps the reagents separated until use. In this scenario, a multiple (dual) chamber bottle equipped with a trigger/pump actuator having a dip (supply) tube inserted in each chamber such that when the trigger/pump actuator is used, aliquots from both chambers are simultaneously drawn and mixed when dispersed. This approach would require a more complex bottle and trigger/actuator due to the multiple product streams.

In view of this, it is desirable to develop a disinfectant or sanitizing or cleaner/deodorizer product that maximizes the stability of the active ingredients so that the product has a suitable shelf-life and is ready to use after manufacturing. Stable products have a longer shelf-life, better consumer appeal, and are easier to use. A stable product can use conventional package that are readily available and cheaper.

SUMMARY

In one aspect, the invention is a device for delivering stabilized chlorine dioxide having improved long term stability by the proper choice of pH. A number of synthesis reactions are known for producing chlorine dioxide. The preferred method is the acidification of chlorite.

The device includes a delivery device configured to deliver a solution to a target application and a stabilized chlorine dioxide (ClO2) product that is configured to be delivered using the delivery device. The chlorine dioxide is produced using a method that includes adding a first amount of Hydrochloric acid (HCl) to a second amount of Sodium chlorite (NaClO2) that is dissolved in water, the first amount being greater than the second amount; agitating the HCL and NaClO2 for at least 10-15 minutes to mix the chemicals and thus allowing the chemical to react to completion; adding a third amount of DOWFAX (i.e., sodium alkyl diphenyloxide disulfonate) to the solution and slowly agitate the HCl, NaClO2 and DOWFAX solution to distribute the DOWFAX; and after the reaction to generate chlorine dioxide (ClO2) in solution has gone to completion, adding a fourth amount of Sodium Hydroxide (NaOH) to adjust the pH of the resulting ClO2 solution to a desired pH and concentration.

In another aspect, the invention is a method of making a high concentration chlorine dioxide with improved long-term stability comprising. The method includes adding 42.61 g/l 10% Hydrochloric acid (HCl) to 3.20 g/l Sodium chlorite (NaClO2) dissolved in water; agitating the HCL and NaClO2 for at least 10-15 minutes to mix the chemicals; adding 1.50 g/l of DOWFAX (i.e., sodium alkyl diphenyloxide disulfonate) and slowly agitate the HCl, NaClO2 and DOWFAX solution to distribute the DOWFAX; and adding 42.23 g/l of 5% Sodium Hydroxide (NaOH) to adjust the pH of the ClO2 solution to a desired pH.

In another aspect, the invention is a method for producing a high concentration chlorine dioxide with improved long-term stability. The method includes 1) adding a molar excess concentration amount of Hydrochloric acid (HCl) to an amount of Sodium chlorite (NaClO2) dissolved in an amount of water; 2) agitating the HCL and NaClO2 until the reaction to form chlorine dioxide (ClO2) is complete; 3) adding an amount of DOWFAX (i.e., sodium alkyl diphenyloxide disulfonate) and slowly agitating the HCl, NaClO2 and DOWFAX solution to distribute the DOWFAX; and 5) adding an amount of Sodium Hydroxide (NaOH) to the ClO2 solution to adjust the pH to a target value; wherein: the molar excess concentration amount of acid=42.61 g/l 10% HCl; the amount of sodium chlorite=3.20 g/l NaClO2

(80%); the amount of DOWFAX=1.50 g/l DOWFAX; the amount of NaOH=42.23 g/l of 5% NaOH; the pH target value approximately 4.5-6.5.

In some embodiments, the delivery device is a spray bottle and the stabilized ClO2 is a sprayable solution; the delivery device is a wipe and the stabilized ClO2 is a solution integrated into the wipe; the delivery device is a tablet and the stabilized ClO2 is integrated into the tablet; the delivery device delivers a laundry detergent and the stabilized ClO2 is integrated into the laundry detergent; the delivery device delivers a deodorizer and the method of producing the ClO2 further comprises adding a fragrance ingredient compatible with ClO2; the delivery device is a cleaning device and the stabilized ClO2 is produced as a concentrate that can be used at full strength or diluted with water.

In some embodiments, the desired pH 4.5-6.5; in some embodiments the desired pH is 5.91. In some embodiment the ClO2 concentration is 1200-1300 PPM. In some embodiment the ClO2 concentration is 1250 PPM In some embodiments, the ClO2 is: a sprayable solution configured to work with a spray bottle; the ClO2 is a concentrated solution configured to be used at full strength or diluted with water prior to use; the method further comprising adding a fragrance ingredient compatible with ClO2 to produce a fragranced solution.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through the use of the accompanying drawings.

DETAILED DESCRIPTION

Figure 1:
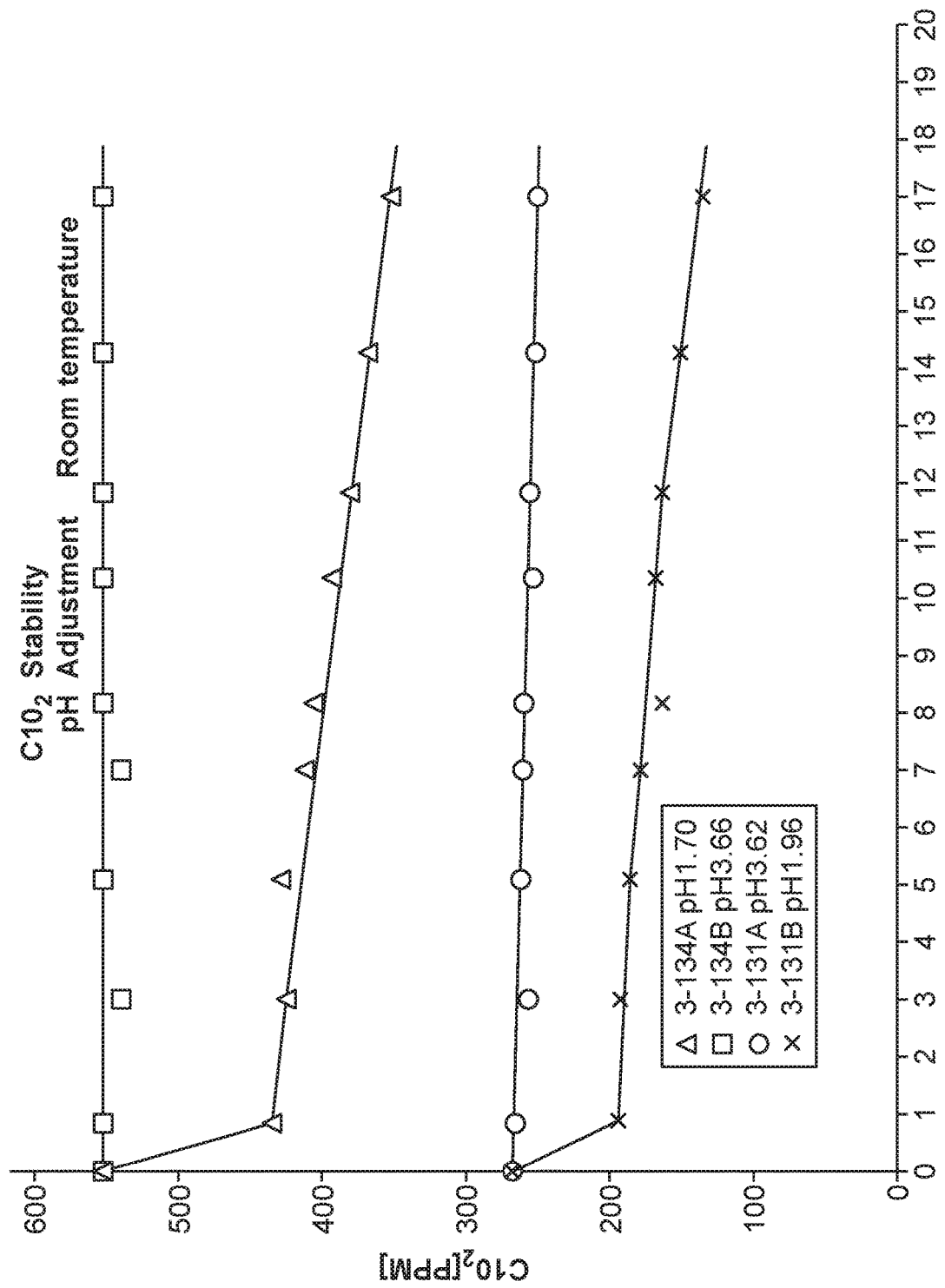
FIG. 1 shows a stability profile of chlorine dioxide compositions with differing pH levels vs. time.

Embodiments of the invention will now be described with reference to the figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The present invention is directed to improve the stability of chlorine dioxide (ClO2) compositions and products. The inventor has found that the stability of the chlorine dioxide can be significantly improved by the proper choice of pH, and through the careful choice of other product formula ingredients. By maximizing the stability of chlorine dioxide, the product has a suitable shelf-life and is ready to use after manufacturing. This stabilization benefit applies regardless of the reaction method used to produce chlorine dioxide.

The improved stability of ClO2 is due to adjusting the pH. The relationship between pH and stability may not be recognized, and that could explain the limited number of ClO2 based product in the market. The increased stability of ClO2 would make a product more desirable than a similar product with limited shelf-life, or a product that must be mixed prior to use.

Chlorine dioxide (ClO2) can be produced by a number of reactions with sodium chlorite (NaClO2). Several industrial methods of synthesis of chlorine dioxide are known such as acidification of chlorite, oxidation of chlorite by chlorine, oxidation of chlorite by persulfate. Other suitable reactions include the reaction of acetic anhydride with chlorite, the reduction of chlorates by acidification in the presence of oxalic acid, and the reduction of chlorates by sulfurous anhydride. Acidification of chlorite according to the following reaction is particularly appealing due to the availability, cost and ease of use of hydrochloric acid. It is understood that regardless of the method used to produce chlorine dioxide, the stability of the solution is controlled by pH and the proper choice of other ingredients.

Any suitable acid may be used in the process disclosed. For example, but not limited to, hydrochloric acid, sulfuric acid, nitric acid, phosphoric acid, acetic acid, citric acid, sulfamic acid, succinic acid, and oxalic acid.

Acids may be moderate to strong acids that are capable of reacting with sodium chlorite to form ClO2. The strongest acids are "mineral acids." Common examples are hydrochloric acid, sulfuric acid, nitric acid, phosphoric acid. These are characterized as having pKa values <1. Strong acids react very quickly with sodium chlorite.

Moderately strong acids include many organic acids. Examples include acetic acid, citric acid, sulfamic acid, succinic acid, and oxalic acid. These are characterized as having pKa values pKa about 5. The acid needs to react with sodium chlorite to form ClO2. If the pka is too high, the reaction will not occur or will be very slow. The lower the pKa, the stronger the acid and the faster the reaction with sodium chlorite.

The process may also include a caustic, such as sodium hydroxide to adjust the solution pH (Reference: Chlorine Dioxide by W. J. Masschelein, Ann Arbor Sciences 1979.)

For example, sodium chlorite (NaClO2) and hydrochloric acid (HCl), shown in Formula (1).

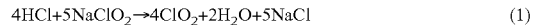

$$4HCl + 5NaClO_2 \rightarrow 4ClO_2 + 2H_2O + 5NaCl \qquad (1)$$

It is generally desirable to have an excess of HCl because it helps speed the reaction and maximizes the conversion of $NaClO_2$ to ClO2. The resulting pH of samples typically produced this way is pH<2.

Example 1

A first batch of ClO2 (3-134), prepared as described in Formula (1) was split into two subsamples. The pH of one subsample was adjusted to pH 3.66 with Sodium Hydroxide (NaOH) (3-134A) and the other subsample was not adjusted and was pH 1.70 (3-134B). A second batch of ClO2 (3-131), prepared as described in Formula (1) at a lower concentration of ClO2 split into two subsamples. The pH of one subsample was adjusted to pH 3.62 (3-131A) and the second subsample was not adjusted and was pH 1.96 (3-131B). The samples were stored in closed amber glass jars. At various times, aliquots were removed and the ClO2 was assayed using the iodometric titration.

FIG. 1 is a plot of the ClO2 concentration vs. time for the samples. As seen in the plot, increasing the pH results in a much more stable product, i.e. slower loss of the ClO2 concentration over time. Raising the sample pH also has the key benefit of preventing the initial rapid drop in ClO2 typically seen in the first few days after synthesis of ClO2. Preventing this initial drop in activity is more cost effective for manufacturing and makes it easier to achieve the desired concentration.

Example 2

Figure 2:
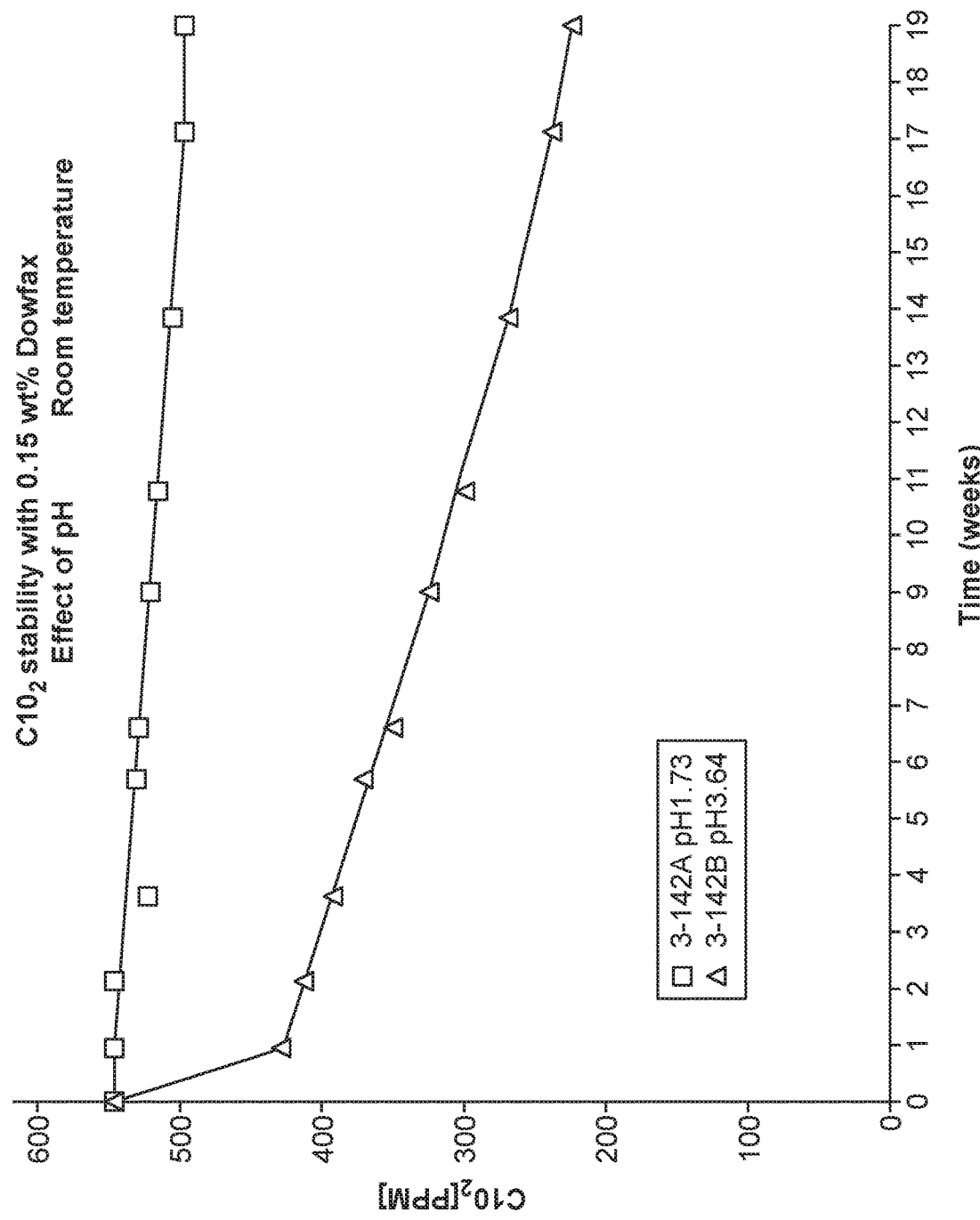
FIG. 2 shows a stability profile of chlorine dioxide and surfactant compositions with differing pH levels vs. time.

FIG. 2 shows a stability profile of another set of samples with surfactant added (3-142), in this case, DOWFAX 3B2 (i.e., sodium alkyl diphenyloxide disulfonate) surfactant. The ClO2 (3-142) was prepared as described in Formula (1) and split into two subsamples. The pH of one subsample was adjusted to pH 3.64 (3-142B) with Sodium Hydroxide (NaOH) and the other subsample was not adjusted and was pH 1.73 (3-134A). Both samples were stored in closed amber glass jars. At various times, aliquots were removed and the ClO2 was assayed using the iodometric titration. FIG. 2 is a plot of the ClO2 concentration with vs. time. This plot again shows increasing the pH to 3.64 results in a much more stable product than the pH 1.73 sample, i.e. slower loss of the ClO2 concentration over time.

Example 3

Figure 3:
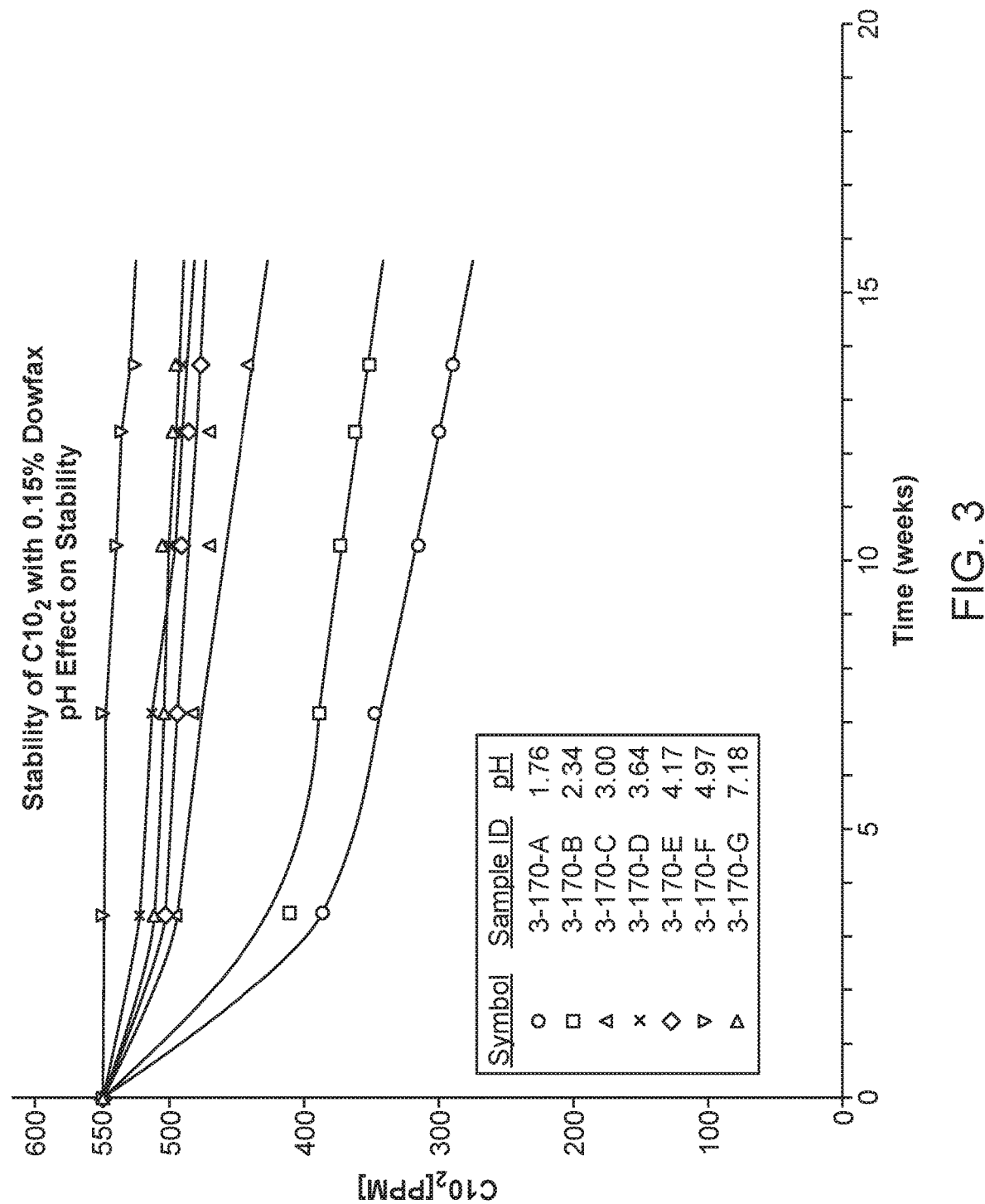
FIG. 3 shows a stability profile of chlorine dioxide and surfactant compositions with differing pH levels vs. time.

FIG. 3 shows a stability profile of another set of samples with surfactant added (3-170), in this case, DOWFAX 3B2 (i.e., sodium alkyl diphenyloxide disulfonate) surfactant. FIG. 3 is similar FIG. 2 but with samples at a broader range in pH. The ClO2 with surfactant was prepared as described and split into seven subsamples. The pH of the first subsample 3-170A was not adjusted and was pH 1.76. The pH of the other subsamples 3-170B to 3-170G were adjusted with Sodium Hydroxide (NaOH). All samples were stored in closed amber glass bottles.

3-170 A pH 1.76
3-170B adjusted to pH 2.34
3-170C adjusted to pH 3.00
3-170D adjusted to pH 3.64
3-170E adjusted to pH 4.17
3-170F adjusted to pH 4.97
3-170G adjusted to pH 7.18

FIG. 3 shows the effect of pH on stability. The graph shows raising the pH in subsamples 3-170B to 3-170G improved stability. However, sample 3-170G with pH 7.18 was not as stable as the samples as pH 4.97 (3-170F), suggesting there may be an optimal pH range for stability where pH ~5 appears to have better stability than pH 3.6.

Example 4

Figure 4:
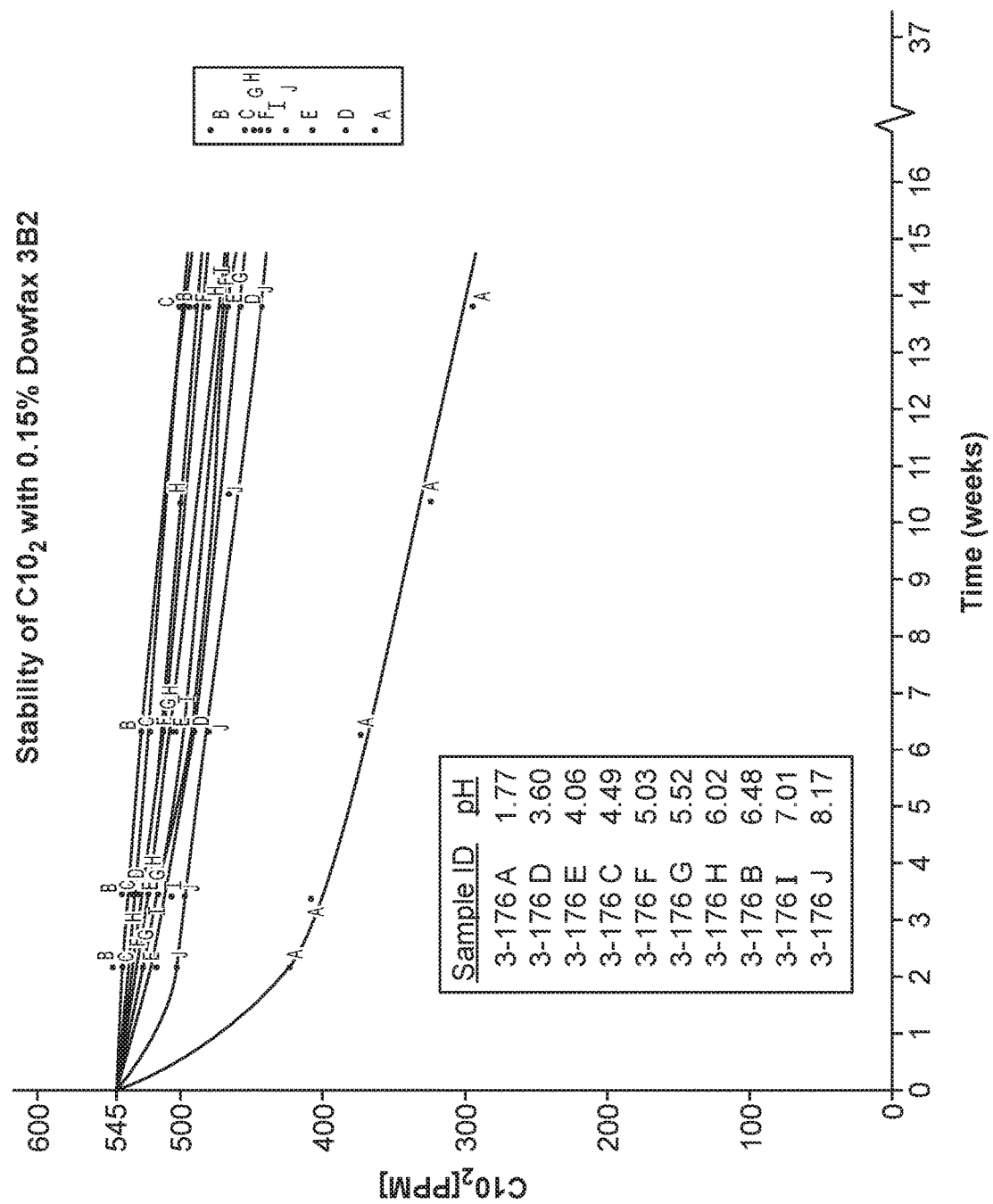
FIG. 4 shows a stability profile for a series of samples with DOWFAX 3B2.

FIG. 4 shows the stability profile for yet another series of samples with DOWFAX 3B2 (i.e., sodium alkyl diphenyloxide disulfonate) (Sample series 3-176A-J). The same procedure was used in preparing the samples. A large sample batch was prepared which was then split into ten sub samples. The pH of the subsamples was adjusted by addition of sodium hydroxide. The samples were stored at room temperature in closed amberglass bottles. At various times, aliquates from the subsamples were removed and the concentration of ClO2 was assayed using an iodometric titration. The sample pH's were checked and adjusted if necessary to the original sample pH. The initial concentration of ClO2 was 545 PPM. Table A shows the concentration of ClO2 and the corresponding calculated percent remaining based on the initial concentration. at 6, 14 and 37 weeks.

TABLE A

| Sample pH | 6 week | | 14 week | | 37 weeks | |
|---|---|---|---|---|---|---|
| | ClO2 PPM | Percent Remaining | ClO2 PPM | Percent Remaining | ClO2 PPM | Percent Remaining |
| 1.77 | 377 | 69.2 | 298 | 54.7 | 162 | 29.8 |
| 3.60 | 493 | 90.4 | 460 | 84.4 | 386 | 70.8 |
| 4.06 | 508 | 93.2 | 460 | 86.1 | 410 | 75.3 |
| 4.49 | 526 | 96.5 | 503 | 92.3 | 459 | 84.2 |
| 5.03 | 515 | 94.5 | 487 | 89.4 | 458 | 84.1 |
| 5.52 | 516 | 94.7 | 484 | 88.8 | 440 | 82.4 |
| 6.02 | 520 | 95.4 | 483 | 88.6 | 451 | 82.8 |
| 6.48 | 528 | 96.9 | 496 | 91.0 | 450 | 82.6 |
| 7.01 | 503 | 92.3 | 473 | 86.8 | 442 | 81.1 |
| 8.17 | 482 | 88.4 | 447 | 82.0 | 427 | 78.3 |

Sample 3-176 A-J

Figure 5:
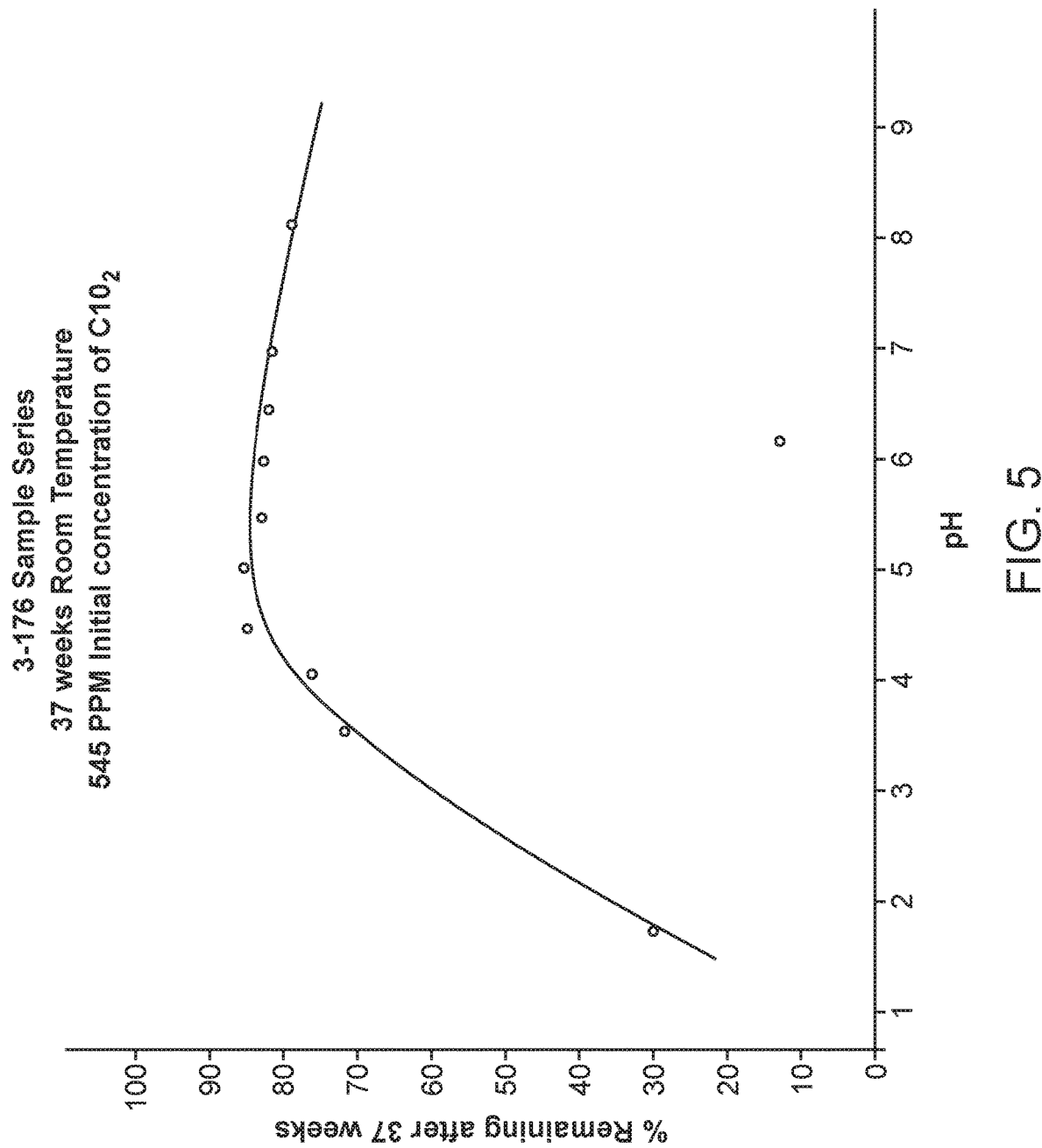
FIG. 5 shows a plot of the percent of ClO2 remaining as a function of pH.

FIG. 5 shows a plot of the percent of ClO2 remaining as a function of pH at the T=37-week data using the data from Table A. The profile shows the improved stability resulting from increasing the samples pH with the optimal pH at ~5 consistent with the data shown in FIG. 4.

General Instructions

All chemicals are used without further purifications. All samples bottles used were amber and appropriately labeled. Each container was rinsed with deionized water before reusing.

All processes and reactions are carried out at room temperature not exceeding (22° C.) unless otherwise specified.

The present invention may be used for various products, including, for example, a surface disinfectant or sanitizer. While the present application discloses embodiments for a surface disinfectant, it is contemplated that the same processes, methods, and solutions may be used for the other products.

Basic Solution

Below is one example of chlorine dioxide based final formulation with improved stability.
1 Hydrochloric acid solution (HCl).
2 Sodium chlorite ($NaClO_2$).
3. Sodium Hydroxide (NaOH)
4 Deionized water ($H_2O$).

Chlorine Dioxide Composition Products Types

Table 1 below shows a base solution composition used for disinfectant/sanitizer solution depicted in FIG. 1 3-134 A/B. As described above, $NaClO_2$ is dissolved in deionized water. The aliquot of 10% HCl was added. The mixture is stirred and allowed to react for 15 minutes. The batch was then split into two 11 subsamples.

TABLE 1

| | pH adjusted Base Solution | | | |
|---|---|---|---|---|
| Product type | 1 | 2 | 3 | 4 |
| Disinfectant | 34.10 g 10% HCL | 2.56 g | See below | 1963 g H2O |

32 g of 5% NaOH was added to a 1 liter sample of 3-134B with a resulting pH of 3.66
32 g of H2O was added to Samples 3-134A to insure the identical volume both samples.
The pH of 3.134A was 1.70.

Surfactant Solution

Below is one example of chlorine dioxide-based formulation having a surfactant with improved stability.
1 Hydrochloric acid solution (HCl).
2 Sodium chlorite (NaClO$_2$).
3. Surfactant (for example, DOWFAX 3B2).
4. Sodium Hydroxide (NaOH)
5 Deionized water (H$_2$O).

Table 2 below shows some example ranges as used in FIG. 2.

TABLE 2

| Product type | pH adjusted with Surfactant (g/liter) | | | | |
| --- | --- | --- | --- | --- | --- |
| | 1 | 2 | 3 | 4 | 5 |
| Disinfectant | 17 g 10% HCL | 1.28 | 1.5 | 16 g 5% NaOH | 980 |

Chlorine dioxide (ClO$_2$) decomposes more quickly when exposed to light, is temperature sensitive and it reacts with many organic compounds. Proper shielding from light and clean production facilities and handling procedures, and material purity are essential to improve stability and avoid unwanted reactions with organic contaminants during production.

The resulting concentration of chlorine dioxide can be tailored to meet the desired biocidal performance. As with many biocidal products, the product of the concentration and the contact time I.e. cxt=constant. As a simplistic approximate relationship, doubling the concentration can result in a reduction of concentration to yield a similar degree of micro efficacy.

Table 3 shows typical ranges of ingredients to produce sanitizer/disinfecting/deodorizing solutions.

TABLE 3

| Component | Wt Percent |
| --- | --- |
| NaClO2 | 0.0050-0.90 |
| HCl | 0.0016-11.00 |
| Surfactant | 0.00-3.00 |
| NaOH | 0-0.90 |
| H$_2$O | balance |
| Total | 100.0 |

It is understood that a practical method of making a very dilute solution of chlorine dioxide, at concentrations as low as 1 PPM, can be prepared by further dilution of a more concentrated solution using deionized water. The lower limit represents the stoichiometric limit from Formula 1.

Higher Product Concentration

The examples described above had a starting concentration of about 550 PPM ClO2. The present invention also contemplates making a solution of chlorine dioxide with higher concentration 1200-1300 PPM having a pH 4.5-6.5 for various applications. The upper limit of HCl assumes a several fold molar excess of HCl to speed the reaction rate.

Table 4 shows an example of ingredients for producing a product having about 1250 PPM ClO2 and Ph 5.91.

TABLE 4

| Component | Wt Percent or | Grams per Liter |
| --- | --- | --- |
| NaClO2 | 0.320 | 3.20 g/l |
| 10% HCl | 4.261 | 42.61 g/l |
| DOWFAX | 0.150 | 1.50 g/l |
| NaOH | 4.230 | 42.23 g/l |
| H$_2$O | balance | balance |
| Total | 100.0 | 100.00 |

A batch of the 1250 PPM ClO2 was prepared as described in Table 4 and was split into two subsamples. The pH of one subsample was not adjusted and was pH 1.50 and the second subsample adjusted using 42.3 gm of 5% NaOH to a pH 5.91.

The sample of the adjusted pH 5.91 and the non-adjusted pH 1.50 formula were titrated at various times out to 8 months. At 8 months, the control non-adjusted pH 1.50 sample lost 92% (8% remaining) and the adjusted pH 5.91 sample lost 27% (74% remaining) activity.

The 550 PPM ClO2 initial concentration losses after 8 months was ~15%. Hence, the percentage of loss increases with concentration even with pH adjusted samples. The limit of how high a concentrated product can be made depends on the amount of acceptable concentration loss over time. It appears that a high concentrated product may be acceptable for if the time period for use is shorter than a lower concentrated product. This may also depend application of the product. While the above sample was 1250 PPM, higher concentrations are also contemplated.

Production Process

The production/manufacturing for the ClO2 based solution should follow general manufacturing guidelines that are typically followed in the production of hypochlorite or peroxide containing based products. All contact surfaces in the production equipment, filling and line and packaging should be in good condition. They must/should be emptied and thoroughly rinsed so as to prevent cross contamination prior to use. Such practices are generally followed in the production of hypochlorite containing products or other products where contamination is undesirable/not tolerated.

Preferably, the entire production process for the solution would be conducted under clean room conditions, in order to minimize the possibility of contamination of the solution by environmental contaminants, such as airborne particles. All contact surfaces, including without limitation surfaces of production equipment, filling equipment and packaging, should be thoroughly cleaned of contaminants prior to use.

Batch Process for Preparation of Chlorine Dioxide

Ranges for the amounts of the Solutions to be used for each embodiment are shown above.

1. Prepare the mixing vessel by decontaminating the container with chlorine dioxide followed by a rinse with deionized water. If the container is used regularly, the container may be rinsed with only deionized water.
2. Add deionized water corresponding to size of the batch followed by the sodium chlorite. Allow the sodium chlorite to completely dissolve. Agitate the sodium chlorite solution.
3. Add the hydrochloric acid to the sodium chlorite solution. After the hydrochloric acid is added, the vessel should be loosely capped to allow the release of any gas that may have formed in the container. The amount of gas formed will vary depending on the concentrations of hydrochloric acid and sodium chlorite present.
4. Allow the acid-chlorite mixture to react for 10-15 minutes with slow agitation.

5. Add the surfactant. Mix or slowly agitate to distribute the surfactant.
6. Adjust the pH with sodium hydroxide solution to achieve the target pH for a stable solution. It is recommended that a pH meter be used to monitor the pH.
7. Store samples in sealed opaque/dark containers.

In the procedure described above, it is also generally acceptable to add the surfactant to the dissolved sodium chlorite before adding the HCl. Allow the chlorite-surfactant-acid mixture to react with slow agitation and then adjust the pH with sodium hydroxide.

Continuous Process Preparation of Solution

Below shows one embodiment of a continuous process for preparing chlorine dioxide Surface Disinfectant.
A. Turn on the water pump in the reactor unit and adjust the deionized water to the desired feed rate.
B. Turn on the chemical solutions feed pumps and set the feed rates to the desired percentage of hydrochloric acid, sodium chlorite and surfactant (optional). The sodium hydroxide can be added downstream to adjust the pH.
C. Assure proper mixing of the water and chemicals.

Dilution—Preparation of Finished Product

Deionized water should be used to prepare or dilute the Solution during production of the finished product. The pH of the finished product should be adjusted to improve stability and/or to achieve the desired product pH. If the product is required to have a specific pH, the overall stability of the ClO2 could subsequently be affected. It is therefore preferred to have the product pH fall within the range of pHs that promotes the improved stability.

Surfactant and Other Adjuncts

Surfactant and other adjuncts can be added to the basic solution to create a range of products. Surfactants such as DOWFAX 3B2 (i.e., sodium alkyl diphenyloxide disulfonate) help facilitate cleaning and wetting of surfaces to improve the micro efficacy of chlorine dioxide. Gum thickeners can be added to thicken the product to improve contact time on a vertical surface or potentially as in a hand sanitizer. For example, gum thickeners may include, but not limited to, xanthan gum, Kelzan AP-AS (from CP Kelco), Keltrol (from CP Kelco) or other suitable gum thickener. The key is that the adjuncts must be reasonably stable with chlorine dioxide. The benefits of proper pH choice also apply to the addition of adjuncts. We are not limited to just these two ingredients. Optimizing the pH will improve stability of formula containing the desired adjuncts.

Concentrated Product

A concentrated product could have applications such as a floor cleaner, general cleaner/deodorizer, use in toilet bowl, or in laundry applications. The concentrated product is a product that may be used full strength or be diluted prior to use. The product is prepared using a stabilized formula and then diluted by adding additional water or adding the concentrated formula to water. An example of a concentrated product and how one is used, is Pine-Sol. You can use Pine-Sol full strength or dilute it. The standard calculations would apply in terms of dilutions i.e. add product to an equal amount of water would dilute it by 50% etc. The concentrate could be a refill for a spray product.

It would also be possible to make a concentrate two-part product where the acid and chlorite are separated until they are combined to react. Since there is no ClO2 produced until acid and chlorite react in a two-part product, the stability issues of ClO2 could be avoided.

The procedure to prepare a ClO2 concentrate is the same as discussed above. We would add excess acid to sodium chlorite, and wait for the reaction to produce ClO2 to go to completion. Surfactant could be present either before or after the reaction of acid and chlorite. Then we would adjust the pH so that the product in the range that provides improved stability. The concentrate is then ready for use.

The concentration of the chlorine dioxide and the surfactant would be higher in the concentrated product to allow for dilution so that the diluted product will still have ingredients to be effective, Higher concentration of ClO2 may be used to sanitize or disinfect while a lower concentration of ClO2 in the diluted form may be good for general cleaning and deodorizing.

The concentrated product should be safe to use and have a suitable shelf life for storage.

In some embodiments the product may include other ingredients, such as fragrance, dyes, or thickeners, etc to change the aesthetics or the form of the product or even change other performance attributes. In some embodiments gum may be added to make a gel product.

Applications for the Product.

It is envisioned that the ClO2 product disclosed herein may be used in many applications and in different products depending on the final dilution and concentration. For example, in some embodiments the (ClO2 product may be used to clean, sanitize and/or disinfect floor, carpet, rug, drapes, bedding and furniture. In some embodiments the ClO2 product may be used for stain removal and cleaning of floor, carpet, rug, furniture, drapes, bedding and other soft fabrics. In some embodiments the ClO2 product may be used for odor control of floor, carpet, rug, furniture and drapes. In some embodiments the ClO2 product may be used for disinfecting and sanitizing drapes, curtains, privacy screens, walls and floors and other materials and surfaces in hospitals. In some embodiments the ClO2 product may be used against pathogens, mold and fungi in healthcare/medical facilities. In some embodiments the ClO2 product may be used for cleaning, sanitizing and disinfecting soft toys, plastic toys, pacifiers, and other baby and childcare equipment, including but not limited to, high chairs, child car seats, push chairs and prams, swings, baby carriers, bikes, scooters, play pens. In some embodiments the ClO2 product may be dispensed in aerosol devices to restrain or disinfect airborne bacteria to improve the indoor air quality.

Other uses of the ClO2 product include sanitizer or disinfectant, floor cleaner, general cleaner/deodorizer, use in toilets, mouthwash or in laundry applications. The product may be used along or combined with other products.

The ClO2 product may be used for floor and carpet/rug cleaning, sanitizing for pets. Some of the advantages of the ClO2 product include:
1) Better Anti Resoiling (pet)—the ClO2 product is better at removing the scents for pets: (it denatures proteins—breaks them down and breaks down other chemicals that are sensitive to powerful oxidation) so therefore will prevent pets from returning to the same spot since they don't recognize the chemicals they left there.
2) Dissipates/Dries Quicker—the ClO2 product doesn't leave a residue since it basically reacts then dissipates into the air or evaporates with like water—it will dry at pretty much the same rate as any other water based cleaner it just won't leave behind a residue like other cleaners.
3) Safe Around Kids And Pets—the ClO2 product is food safe so you can feel confident the solution is okay for kids and pets to be around.
4) Odor Elimination—the ClO2 product denatures proteins—breaks them down and breaks down other chemicals that are sensitive to powerful oxidation—almost anything that has an odor is prone to oxidation—therefore scents can be eliminated.

5) More Effective On Germ Kill—the ClO2 product is the most powerful oxidizer available and destroys germs like other chemicals mentioned above.

6) Safe On Carpets And Fabrics—the ClO2 product may be used on because most carpets and fabrics today have dyes that are resistant to the oxidation from cleaners.

7) No Discoloring—the ClO2 product does not discolor.

8) Environmentally Friendly—the ClO2 product does not leave a residue nor does it create a carcinogenic residue as a byproduct of reaction like other germ kill products such as sodium hypochlorite does.

It is envisioned that the ClO2 product be delivered in many different forms using many different devices or applicators for delivery, depending on the application. Below are some non-limiting examples, Sanitizer or Disinfectant—For hard surfaces, the ClO2 product may be packaged in a spray bottle or package of wipes. For hand sanitizer, the ClO2 product be in a squirt bottle. For soft surfaces, the ClO2 product may be provided in a concentrated solution either at full concentration or diluted that can be used/applied with a cleaning machine, such as a carpet cleaner, vacuum, floor cleaner, steam cleaner, or other cleaning/disinfection machine.

Floor Cleaner—The ClO2 product may be provided in a concentrated solution that can be used either at full concentration or diluted, such as Pine-Sol. The ClO2 product may be applied using a cleaning machine, such as a hard floor cleaner or sweeper capable of delivering fluids to the floor.

General cleaner/deodorizer—The ClO2 product may be provided in a spray bottle, like Lysol, or disinfecting wipes like Clorox Wipes.

Toilet—The ClO2 product may be provided in a tablet form to drop-in the bowl or put in the toilet tank for each flush, like Clorox tablets. The tables may be different concentration, such as the drop-in bowl tablet may have a higher concentration than the tank tablet.

Laundry—The ClO2 product may be mixed in a laundry detergent, or may be a separate solution additive, like Lysol Laundry Sanitizer Additive, or as beads that are thrown in the wash, like Downy Fresh Scent Booster Beads.

In some embodiments the present invention is directed to improve the stability of chlorine dioxide (ClO2) compositions and products by the proper choice of pH, and through the careful choice of other product formula ingredients. By maximizing the stability of chlorine dioxide, the product has a suitable shelf-life and is ready to use after manufacturing.

In some embodiments the device includes a delivery device configured to deliver a solution to a target application and a stabilized chlorine dioxide (ClO2) product that is configured to be delivered using the delivery device. The chlorine dioxide is produced using a method that includes adding a first amount of Hydrochloric acid (HCl) to a second amount of Sodium chlorite (NaClO2) that is dissolved in water, the first amount being greater than the second amount; agitating the HCL and NaClO2 for at least 10-15 minutes to mix the chemicals and thus allowing the chemical to react to completion; adding a third amount of DOWFAX to the solution and slowly agitate the HCl, NaClO2 and DOWFAX solution to distribute the DOWFAX; and after the reaction to generate chlorine dioxide (ClO2) in solution has gone to completion, adding a fourth amount of Sodium Hydroxide (NaOH) to adjust the pH of the resulting ClO2 solution to a desired pH and concentration.

In some embodiments the invention is a method of making a high concentration chlorine dioxide with improved long-term stability comprising. The method includes adding 42.61 g/l 10% Hydrochloric acid (HCl) to 3.20 g/l Sodium chlorite (NaClO2) dissolved in water; agitating the HCL and NaClO2 for at least 10-15 minutes to mix the chemicals; adding 1.50 g/l of DOWFAX and slowly agitate the HCl, NaClO2 and DOWFAX solution to distribute the DOWFAX; and adding 42.23 g/l of 5% Sodium Hydroxide (NaOH) to adjust the pH of the ClO2 solution to a desired pH.

In some embodiments the invention is a method for producing a high concentration chlorine dioxide with improved long-term stability. The method includes 1) adding a molar excess concentration amount of Hydrochloric acid (HCl) to an amount of Sodium chlorite (NaClO2) dissolved in an amount of water; 2) agitating the HCL and NaClO2 until the reaction to form chlorine dioxide (ClO2) is complete; 3) adding an amount of DOWFAX, 4) slowly agitating the HCl, NaClO2 and DOWFAX solution to distribute the DOWFAX; and 5) adding an amount of Sodium Hydroxide (NaOH) to the ClO2 solution to adjust the pH to a target value; wherein: the molar excess concentration amount of acid=42.61 g/l 10% HCl; the amount of sodium chlorite=3.20 g/l NaClO2 (80%); the amount of DOWFAX=1.50 g/l DOWFAX, the amount of NaOH=42.23 g/l of 5% NaOH; the pH target value approximately 4.5-6.5.

In some embodiments, the delivery device is a spray bottle and the stabilized ClO2 is a sprayable solution; the delivery device is a wipe and the stabilized ClO2 is a solution integrated into the wipe; the delivery device is a tablet and the stabilized ClO2 is integrated into the tablet; the delivery device delivers a laundry detergent and the stabilized ClO2 is integrated into the laundry detergent; the delivery device delivers a deodorizer and the method of producing the ClO2 further comprises adding a fragrance ingredient compatible with ClO2; the delivery device is a cleaning device and the stabilized ClO2 is produced as a concentrate that can be used at full strength or diluted with water.

In some embodiments, the desired pH is 4.5-6.5, and in other embodiments the desired pH is 5.91.

In some embodiments, the ClO2 is: a sprayable solution configured to work with a spray bottle; the ClO2 is a concentrated solution configured to be used at full strength or diluted with water prior to use; the method further comprising adding a fragrance ingredient compatible with ClO2 to produce a fragranced solution.

It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claims set forth herebelow not be construed as being order-specific unless such order specificity is expressly stated in the claim.

The invention claimed is:

1. A device for delivering stabilized chlorine dioxide comprising:
   a stabilized chlorine dioxide (ClO2) product produced for a target application using a method comprising:
      adding a first amount of Hydrochloric acid (HCl) to a second amount of Sodium chlorite (NaClO$_2$) that is dissolved in water, the first amount being greater than the second amount;

agitating the HCL and NaClO2 for at least 10-15 minutes to mix the chemicals and thus allowing the chemical to react to completion; and adding a third amount of Sodium dodecyl diphenyloxide disulfonate to the solution and slowly agitate the HCl, NaClO2 and Sodium dodecyl diphenyloxide disulfonate solution to distribute the Sodium dodecyl diphenyloxide disulfonate; and after the reaction to generate chlorine dioxide (ClO2) in solution has gone to completion, adding a fourth amount of Sodium Hydroxide (NaOH) to adjust the pH of the resulting ClO2 solution to a desired pH and ClO2 concentration; and a delivery device configured to deliver stabilized chlorine dioxide (ClO2).

2. The device of claim 1, wherein the target application is a stabilized chlorine dioxide formulated to clean, sanitize and/or disinfect floor, carpet, rug, drapes, bedding and furniture.

3. The device of claim 1, wherein the target application is a stabilized chlorine dioxide formulated for stain removal and cleaning of floor, carpet, rug, furniture, drapes, bedding and other soft fabrics.

4. The device of claim 1, wherein the target application is a stabilized chlorine dioxide formulated for odor control of floor, carpet, rug, furniture and drapes.

5. The device of claim 1, wherein the target application is a stabilized chlorine dioxide formulated for disinfecting and sanitizing drapes, curtains, privacy screens, walls and floors and other materials and surfaces in hospitals.

6. The device of claim 1, wherein the target application is a stabilized chlorine dioxide formulated for use against pathogens, mold and fungi in healthcare/medical facilities.

7. The device of claim 1, wherein the target application is a stabilized chlorine dioxide formulated for cleaning, sanitizing and disinfecting soft toys, plastic toys, pacifiers, and other baby and childcare equipment, including but not limited to, high chairs, child car seats, push chairs and prams, swings, baby carriers, bikes, scooters, play pens.

8. The device of claim 1, wherein the target application is a stabilized chlorine dioxide formulated to denature proteins and breaks down other chemicals that are sensitive to powerful oxidation to prevent pets from resoiling the same area.

9. The device of claim 1, wherein the delivery device is a spray bottle and the stabilized ClO2 is a sprayable solution.

10. The device of claim 1, wherein the stabilized ClO2 is produced as a concentrate that can be used at full strength or diluted with water.

11. The device of claim 1, wherein the delivery device is an aerosol device and the stabilized ClO2 is produced to treat airborne bacteria to improve the indoor air quality.

12. The device of claim 1, wherein:
the first amount=17 g/l 10% HCl;
the second amount=1.28 g/l NaClO2 (80%) dissolved in water;
the third amount=1.50 g/l Sodium dodecyl diphenyloxide disulfonate;
the fourth amount=36.2 g/l of 5% NaOH;
pH target value approximately 5;
ClO2 concentration approximately 500 ppm.

13. The device of claim 1, wherein:
the first amount=42.61 g/l 10% HCl;
the second amount=3.20 g/l NaClO2 dissolved in water;
the third amount=1.50 g/l Sodium dodecyl diphenyloxide disulfonate;
the fourth amount=42.23 g/l of 5% NaOH;
ClO2 concentration approximately 1200-1300 PPM;
pH target value approximately 4.5-6.5.

14. The device of claim 1, wherein the ClO2 concentration is 1200-1300 PPM.

15. The device of claim 1, wherein the desired pH is 4.5-6.5.

16. The device of claim 1, further comprising adding a fragrance ingredient compatible with ClO2 to produce a fragranced solution.

17. The device of claim 1, wherein the stabilized ClO2 is produced as a concentrate used as a refill for a spray product that can be used at full strength or diluted with water.

* * * * *